(12) United States Patent
Collins et al.

(10) Patent No.: US 11,141,297 B2
(45) Date of Patent: Oct. 12, 2021

(54) ENDOVASCULAR DELIVERY DEVICE HAVING AN IMPROVED TOP-CAP ASSEMBLY

(71) Applicant: Cook Medical Technologies LLC, Bloomington, IN (US)

(72) Inventors: James Collins, Paddington (AU); William Parke, Paddington (AU); Logan Smith, Mount Gravatt (AU)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 93 days.

(21) Appl. No.: 16/225,025

(22) Filed: Dec. 19, 2018

(65) Prior Publication Data
US 2020/0197201 A1 Jun. 25, 2020

(30) Foreign Application Priority Data
Dec. 19, 2018 (AU) ................................ 2018282309

(51) Int. Cl.
*A61F 2/95* (2013.01)
*A61F 2/07* (2013.01)
*A61F 2/848* (2013.01)

(52) U.S. Cl.
CPC .................. *A61F 2/95* (2013.01); *A61F 2/07* (2013.01); *A61F 2/848* (2013.01); *A61F 2/9517* (2020.05);
(Continued)

(58) Field of Classification Search
CPC .... A61F 2/95; A61F 2/07; A61F 2/848; A61F 2/9517; A61F 2/2427; A61F 2/2466;
(Continued)

(56) References Cited

U.S. PATENT DOCUMENTS 5,391,172 A 2/1995 Williams et al.
5,415,664 A 5/1995 Pinchuk
(Continued)

FOREIGN PATENT DOCUMENTS

AU 2014200686 B1 6/2014
AU 2018282309 2/2019
(Continued)

*Primary Examiner* — Erich G Herbermann
(74) *Attorney, Agent, or Firm* — Crowell & Moring LLP

(57) ABSTRACT

An endovascular delivery device is disclosed. The device comprises a handle assembly at a distal end thereof and a top-cap assembly at a proximal end thereof. The top-cap assembly has an open configuration and a closed configuration and comprises: a capsule comprising an inner portion and an outer tubular portion and defining a cavity within the outer tubular portion, the cavity receiving the proximal portion of the endograft in the open configuration; and a retriever assembly having a body portion arranged and constructed to fit within the cavity of the capsule in the closed configuration. The device further comprises: a guide wire catheter extending through the handle assembly, the guide wire catheter being affixed at a proximal end thereof to the top-cap assembly; and an endograft receiving portion extending distally with respect to the top-cap assembly. In the closed configuration, the cavity is closed by the body portion of the retriever assembly.

20 Claims, 21 Drawing Sheets

(52) U.S. Cl.
CPC .............. *A61F 2002/8483* (2013.01); *A61F 2002/9528* (2013.01); *A61F 2002/9534* (2013.01)

(58) Field of Classification Search
CPC .................. A61F 2/9522; A61F 2/962; A61F 2002/8483; A61F 2002/9528; A61F 2002/9534; A61F 2002/9505; A61F 2002/9511; A61F 2002/9583
See application file for complete search history.

(56) References Cited

U.S. PATENT DOCUMENTS

| | | |
|---|---|---|
| 7,435,253 B1 | 10/2008 | Hartley et al. |
| 8,372,132 B2 | 2/2013 | Shin et al. |
| 8,641,749 B2 | 2/2014 | Barthold et al. |
| 8,721,714 B2 | 5/2014 | Kelley |
| 9,486,350 B2 | 11/2016 | Argentine |
| 9,622,893 B2* | 4/2017 | Huser ................ A61F 2/966 |
| 2008/0221666 A1* | 9/2008 | Licata ..................... A61F 2/95 |
| | | 623/1.22 |
| 2013/0274859 A1 | 10/2013 | Argentine |

FOREIGN PATENT DOCUMENTS

| | | |
|---|---|---|
| AU | 2017904881 | 6/2019 |
| EP | 3494936 A1 | 6/2019 |
| WO | 2016123557 A1 | 8/2016 |

* cited by examiner

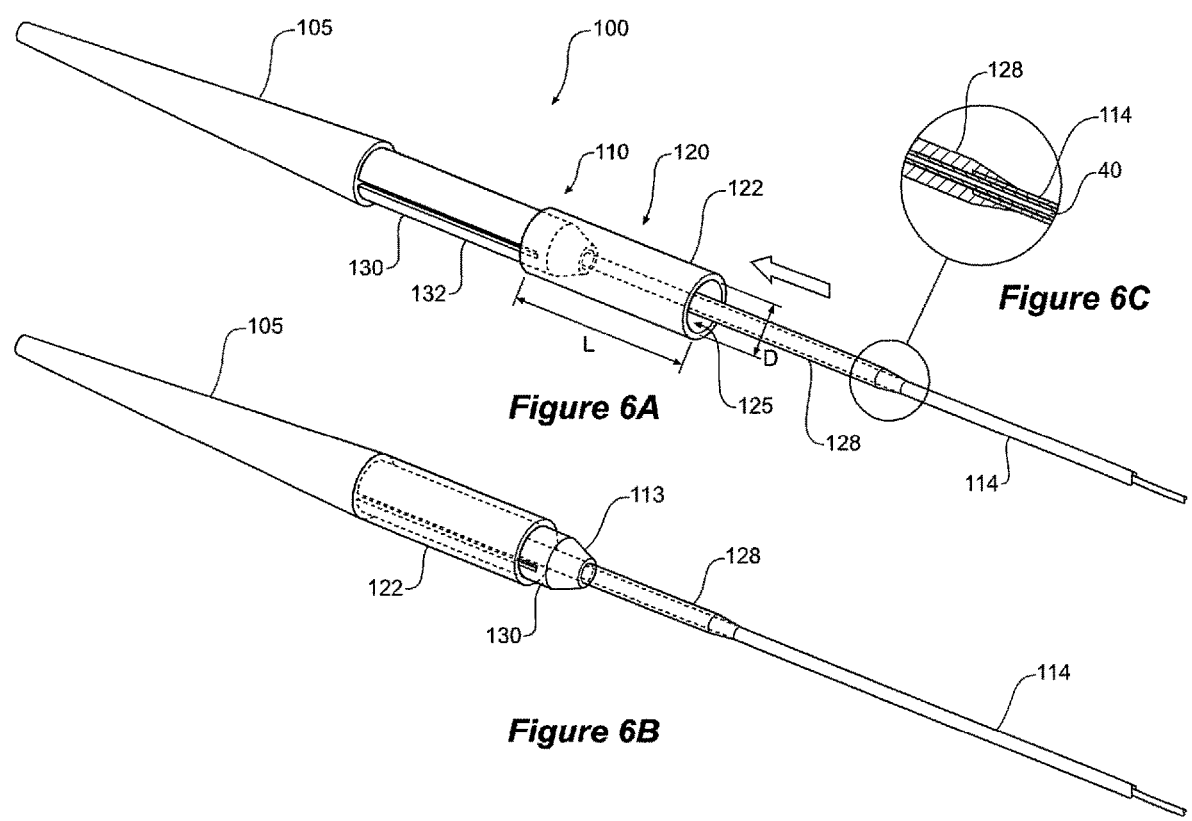

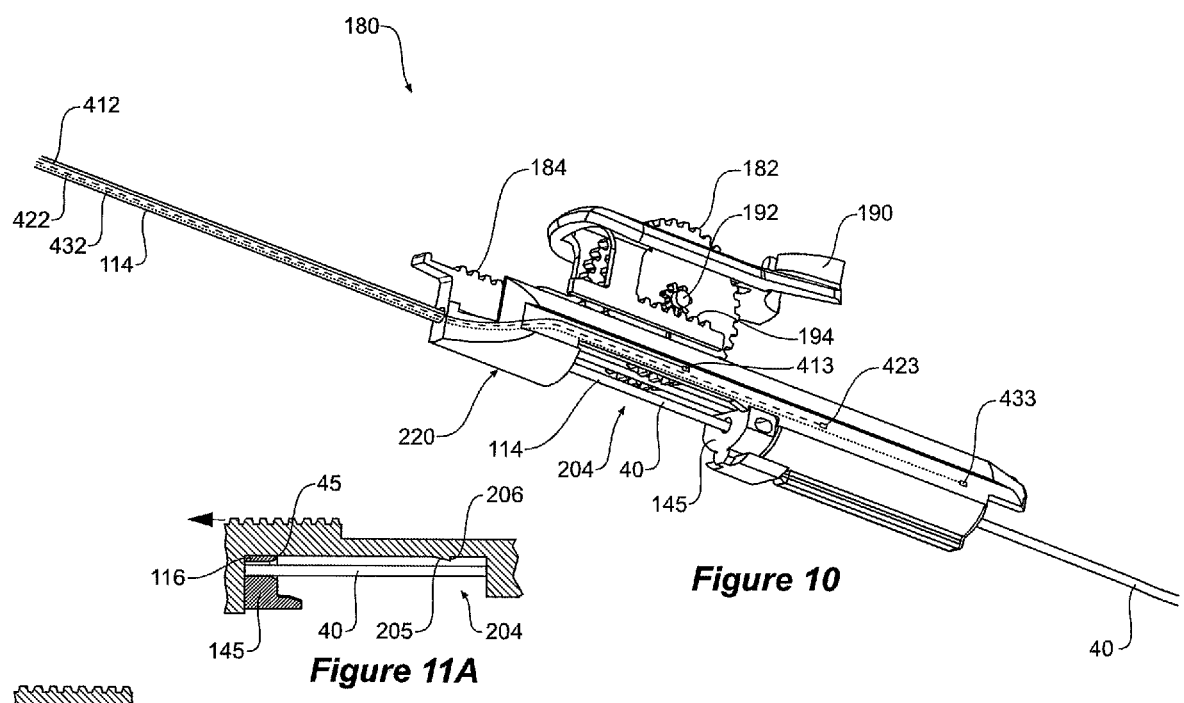

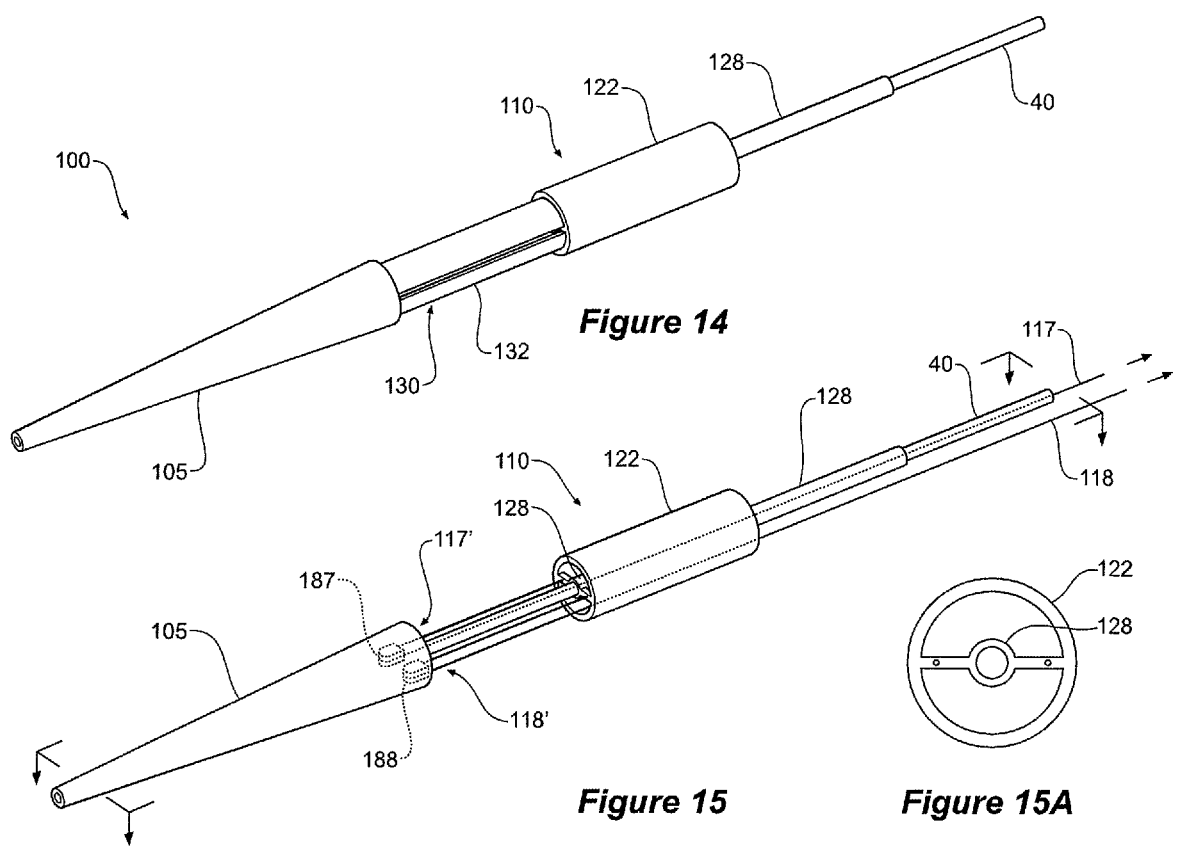

ENDOVASCULAR DELIVERY DEVICE HAVING AN IMPROVED TOP-CAP ASSEMBLY

CROSS REFERENCE TO RELATED APPLICATIONS

This application claims the benefit of Australian patent application No. 2018282309 filed on Dec. 19, 2018 entitled "AN ENDOVASCULAR DELIVERY DEVICE HAVING AN IMPROVED TOP-CAP ASSEMBLY" the entire contents of which are incorporated herein by reference.

FIELD OF THE INVENTION

The present invention relates to endografts and their delivery systems, sometimes referred to as endoluminal delivery device assemblies. In particular, the present invention relates to endoluminal delivery device assemblies capable of delivering prostheses, endografts or stent grafts into the vascular system of humans or animals.

BACKGROUND OF THE INVENTION

Stent graft and delivery devices are used in aortic intervention. They are used by vascular surgeons to treat aneurysms and to repair regions of the aorta, including the aortic arch, the thoracic aorta, the abdominal aorta and the aortic bifurcation.

Delivery devices allow deployment of intraluminal prostheses or endografts into the lumen of a patient from a remote location.

Numerous devises and procedures have been developed that involve the percutaneous insertion of a prosthesis into a body lumen, such as a blood vessel or duct, of a patient's body. Such a prosthesis may be introduced into the lumen by a variety of known techniques. For example, a wire guide may be introduced into a blood vessel using the Seldinger technique. This technique involves creating a surgical opening in the vessel with a needle and inserting a wire guide into the vessel through a bore of the needle. The needle can be withdrawn, leaving the wire guide in place. A delivery device is then inserted over the wire guide and into the vessel. The delivery device may be used in conventional fashion to insert into the blood vessel a variety of prostheses, such as stents, stent grafts, catheters, cardiac leads, balloons, and the like.

For example, the delivery device may be used to deliver and deploy an expandable prosthesis, such as a stent graft, to an aneurysmal blood vessel site. A stent graft is usually formed from a tubular body of a biocompatible graft material with one or more stents mounted into or onto the tubular body to provide support therefor. The stents may be balloon expandable stents and/or self-expanding stents. The deployment of the prosthesis into the lumen of a patient from a remote location by the use of an introducer delivery and deployment device is described in, for example, U.S. Pat. No. 7,435,253 to Hartley entitled "A Prosthesis and a Method and Means of Deploying a Prosthesis", which is incorporated herein by reference in its entirety.

Delivery devices are configured to retain a prosthesis in a delivery configuration during delivery to the desired deployment site. The delivery catheter typically includes an inner catheter/cannula spaced from an outer sheath to define a prosthesis retaining region for receiving the prosthesis. The prosthesis is loaded onto an inner cannula along a prosthesis retaining region, with an outer sheath retaining the prosthesis in the delivery configuration. After the delivery device is delivered to the desired deployment site, the prosthesis may be deployed, for example, with retraction of the outer sheath relative to the inner cannula away from the prosthesis to allow for expansion thereof. Accurate placement of an appropriately sized prosthesis generally sufficiently covers the target site for treatment and the ends of the prosthesis are typically engaged with healthy tissue of the body lumen.

Some delivery devices include a top-cap assembly at an end thereof. Such top-cap assemblies are provided to retain an end of an expandable prosthesis, such as a stent graft, before it is finally deployed into a bodily lumen such as the aorta. Top-cap assemblies are known to include a cavity for receiving an end of an expandable prosthesis, such as a stent graft.

One form of delivery device uses a proximal nose cone with a distally facing capsule to encompass an exposed stent and barbs extending from the exposed stent during delivery. After the stent graft has been released and the capsule has been removed from the exposed stent, the capsule along with the delivery device must be withdrawn. The capsule, however, typically has a distally facing opening or mouth with an edge surrounding it and this edge can engage with stents of the deployed stent graft and potentially cause problems by dislodging the stent graft from its position on the wall of the lumen.

Desirably, the cavity or mouth of the capsules described above are filled or covered before the delivery device is removed, thereby reducing the likelihood of the delivery device catching on the deployed prosthesis or on any parts of the body including its vascular system.

Prior art top-cap assemblies include components and mechanisms for advancing the tip of the delivery device so as to close or cover the cavity or mouth of the capsule. While this can be advantageous for releasing the stent graft, it has some disadvantages.

Various locking mechanisms have been developed to ensure that the cavity or mouth of the capsule remains covered or closed during withdrawal of the delivery device.

It is an object of the invention to provide an improved endograft and delivery device assembly.

Throughout this specification, the term "distal" with respect to a portion of the aorta, a deployment device or an endograft means the end of the aorta, deployment device or endograft further away in the direction of blood flow from the heart and the term "proximal" means the portion of the aorta deployment device or end of the endograft nearer to the heart in the direction of blood flow.

SUMMARY OF THE INVENTION

According to an aspect of the invention, an endovascular delivery device, for delivering an endograft having an exposed stent, is provided. The delivery device comprises:
  a handle assembly at a distal end thereof;
  a top-cap assembly at a proximal end thereof, the top-cap assembly having an open configuration and a closed configuration, the top-cap assembly comprising:
    a capsule comprising an inner portion and an outer tubular portion and defining a cavity within the outer tubular portion, the cavity receiving a proximal portion of the endograft in the open configuration; and
    a retriever assembly having a body portion, the body portion arranged and constructed to fit within the cavity of the capsule in the closed configuration;

a guide wire catheter extending through the handle assembly, the guide wire catheter being affixed at a proximal end thereof to the top-cap assembly; and an endograft receiving portion extending distally with respect to the top-cap assembly, whereby in the closed configuration, the cavity is closed by the body portion of the retriever assembly, whereby the outer tubular portion extends distally beyond the body portion when in the open configuration to hold compressed a length of the exposed stent of the endograft.

In one form, the extent to which the outer tubular portion extends distally beyond the body portion for a length L such that L/D is at least 2, when in the open configuration, where D is an internal diameter of the cavity.

In one form, L/D is at least 3, when in the open configuration.

In one form, the inner portion and the outer tubular portion are joined by a radially extending joiner portion, the joiner portion extending through at least one elongate longitudinally extending slot within the body portion of the retriever assembly, thereby allowing the top-cap assembly to slide from the open configuration to the closed configuration.

In one form, the body portion of the retriever assembly comprises a tapered distal end portion, the tapered distal end portion tapering in a distal direction.

In one form, the device further comprises a connector extending from the top-cap assembly to the handle assembly, the connector arranged to transfer motion from the handle assembly to the top-cap assembly so as to slide the top-cap assembly from its open configuration to its closed configuration.

In one form, the proximal portion of the endograft comprises a plurality of barbs.

In one form, the barbs of the endograft are covered by the outer tubular portion when in the open configuration.

In one form, wherein the top-cap assembly comprises a tip, the tip tapering in a proximal direction.

In one form, the guide wire cannula is attached to the tip of a proximal end thereof.

The device as claimed in claim 1 mounted within a sheath assembly, the sheath assembly comprising a seal housing assembly and a sheath extending proximally from the seal housing assembly.

In one form, the device is mounted within a sheath assembly, wherein the sheath comprises a proximal end that is positionable over the capsule.

In one form, the cavity is annular in shape.

In one form, the connector comprises an elongate tube co-axially mounted over the guide wire catheter.

In an alternative form, the connector comprises at least one wire mounted adjacent the guide wire catheter, the wire having a distal portion connected to the handle assembly and a proximal portion looped over at least one corresponding return surface on the top-cap assembly and extending distally back to the capsule, the wire joined to the capsule such that as the handle assembly creates a pulling displacement of the distal portion of the wire, the capsule is drawn over the body portion of the retriever assembly thereby moving the top-cap assembly towards its closed configuration.

In one form, the connector comprises two wires mounted adjacent the guide wire catheter and two return surfaces on the top-cap assembly, a first of two wires looping over a corresponding first of the two return surfaces, and a second of two wires looping over a corresponding second of the two return surfaces.

According to another aspect of the invention, an endovascular delivery device, for delivering an endograft, is provided, the delivery device comprising:

a handle assembly at a distal end thereof;

a top-cap assembly at a proximal end thereof, the top-cap assembly having an open configuration and a closed configuration, the top-cap assembly comprising:

a capsule comprising an inner portion and an outer tubular portion and defining a cavity within the outer tubular portion, the cavity having an annular shape and receiving a proximal portion of the endograft in the open configuration, thereby covering the barbs; and a retriever assembly having a body portion, the body portion arranged and constructed to fit within the cavity of the capsule in the closed configuration;

a guide wire catheter extending through the handle assembly, the guide wire catheter being affixed at a proximal end thereof to the top-cap assembly;

an endograft receiving portion extending distally with respect to the top-cap assembly, whereby in the closed configuration, the cavity is closed by the body portion of the retriever assembly; and a connector extending from the top-cap assembly to the handle assembly, the connector arranged to transfer motion from the handle assembly to the top-cap assembly so as to slide the top-cap assembly from its open configuration to its closed configuration, whereby the outer tubular portion extends distally beyond the body portion when in the open configuration, and wherein the inner portion and the outer tubular portion are joined by a radially extending joiner portion, the joiner portion extending through at least one elongate longitudinally extending slot within the body portion of the retriever assembly, thereby allowing the top-cap assembly to slide from the open configuration to the closed configuration.

BRIEF DESCRIPTION OF DRAWINGS

Embodiments of the present invention will be discussed with reference to the accompanying drawings wherein:

FIG. 6A shows a tip assembly at an end of the device of FIG. 5A in an isometric view, the tip assembly having a top-cap assembly, the top-cap assembly shown in an open configuration;

FIG. 6B is the same as FIG. 6A, but shows the top-cap assembly shown in a closed configuration;

FIG. 6C is a close up view of a portion of the device shown in FIGS. 6A and 6B;

FIG. 10 is an isometric view of components of the handle assembly of FIG. 1A;

FIGS. 11A and 11B are close up views of a portion of FIG. 10 in two different positions;

FIG. 14 shows a tip assembly of a third embodiment of the invention at an end of the device of the type shown in FIG. 1A in an isometric view. In this view, the tip assembly has a top-cap assembly in an open configuration;

FIG. 15 is similar to FIG. 14, but the retriever assembly is omitted to show internal wires;

FIG. 15A is an end view of the capsule shown in FIG. 15;

DESCRIPTION OF EMBODIMENTS

Figure 1A:
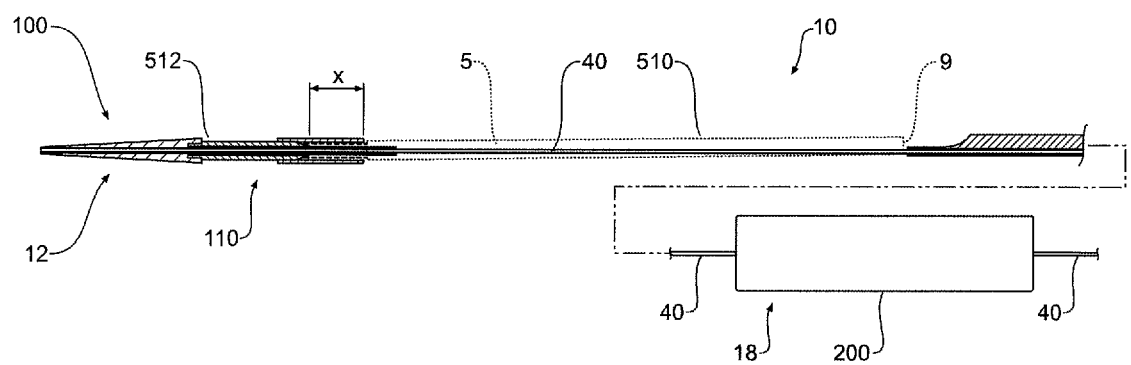
FIG. 1A shows a first embodiment of an endoluminal delivery device according to the invention in a side view.

For the purposes of understanding the principles of the invention, reference will now be made to the embodiments illustrated in the drawings, and specific language will be used to describe them. It is to be understood that the Figures are, in some cases, schematic and do not show the various components in their actual scale. In many instances, the Figures show scaled up components to assist the reader.

Referring now to FIGS. 1A, 1B, 2A and 2B, there is shown an endovascular delivery device 10 for the percutaneous insertion into the artery (or other bodily lumen) of prostheses such as stents, stent grafts, catheters, cardiac leads, balloons, and the like, according to a first embodiment of the invention. In FIGS. 1A, 1B, 2A and 2B, a prosthesis in the form of endograft 5 is shown. The endograft 5 has a proximal portion 6 and a distal portion 9, as is most clearly shown in FIG. 2A. The endograft 5 shown is a stent graft having a plurality of stents including an exposed stent 7, shown in FIG. 2A (the stent graft 5 may also include external and internal stents such as the external stent 4 and internal stent 3 shown in FIGS. 8B and 8C).

Referring again to FIGS. 1A, 1B, 2A, 2B, 3A, 3B, 4A to 4C, it can be seen that the endovascular delivery device 10 comprises: a handle assembly 200 at a distal end 18 thereof and a top-cap assembly 110 at a proximal end 12 thereof. The top-cap assembly has an open configuration and a closed configuration shown in FIGS. 3A and 3B respectively. The top-cap assembly comprises: a capsule 120 comprising an inner portion 128 and an outer tubular portion 122 and defining a cavity 125 within the outer tubular portion, as is most clearly shown in FIGS. 3A and 4C. With the embodiment shown, the cavity 125 is of an annular shape. In other embodiments, not shown, the cavity may have a different shape. Alternative shapes that are able to receive the proximal portion 6 of the endograft 5 in the open configuration may be provided.

Figure 2A:
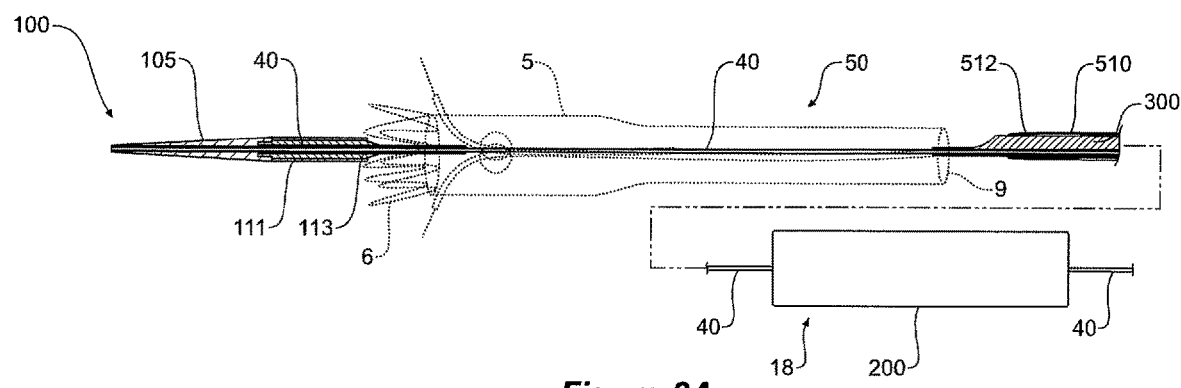
FIG. 2A is a similar side view to that of FIG. 1A but showing a sheath assembly in a retracted position.
Figure 2B:
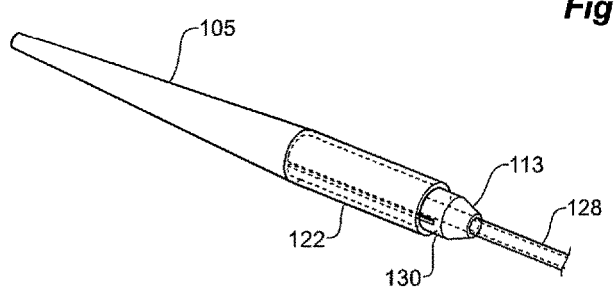
FIG. 2B shows a proximal end of the assembly of FIG. 2A.
Figure 3A:
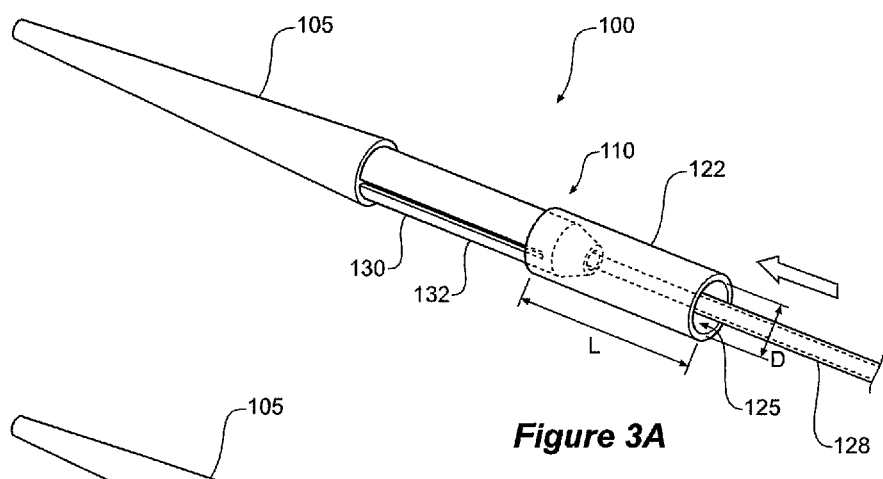
FIG. 3A shows a tip assembly at an end of the device of FIG. 1A in an isometric view, the tip assembly having a top-cap assembly, the top-cap assembly shown in an open configuration.
Figure 3B:
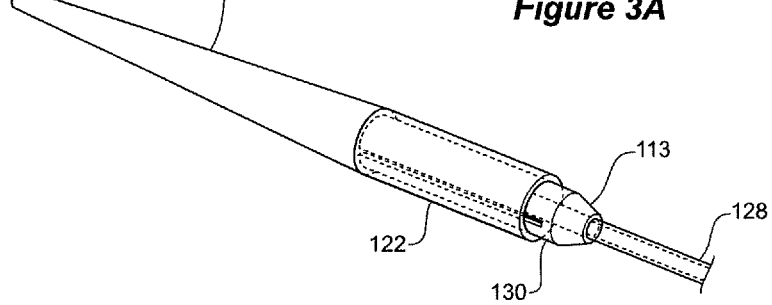
FIG. 3B is the same as FIG. 3A, but shows the top-cap assembly shown in a closed configuration.
Figure 4A:
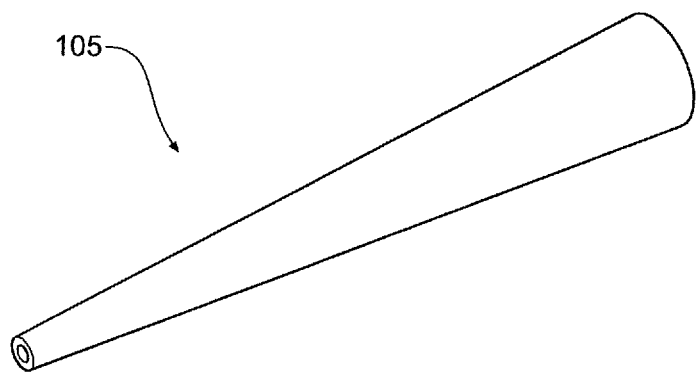
FIGS. 4A to 4C show components of the tip assembly of FIGS. 3A and 3B.
Figure 4B:
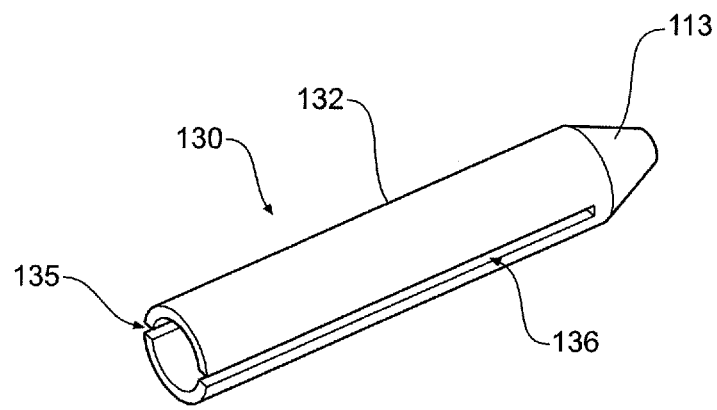

The top-cap assembly of FIGS. 1A, 1B, 2A, 2B, 3A, 3B, 4A to 4C further comprises a tip 105, the tip tapering in a proximal direction. In FIG. 4A, this tip 105 is shown as a separate component from the retriever assembly 130 shown in FIG. 4B. The tip 105 and the retriever assembly 130 will generally be fabricated as separate components and then glued together, however they may be fabricated as a unitary component. That is, the tip 105 may be integral with the tip retriever assembly 130.

Figure 4C:
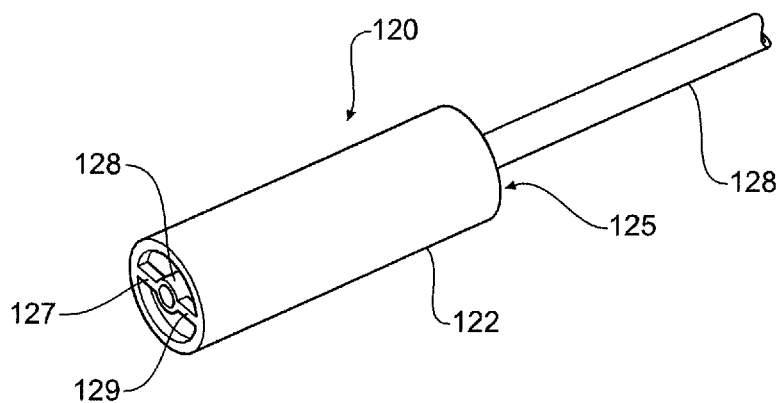

In FIG. 4C, a proximal end of the inner portion 128 can be seen. FIG. 4C also clearly shows the outer tubular portion 122 and the capsule 120. The inner portion 128 and the outer tubular portion 122 are joined by radially extending joiner portions 127 and 129, the joiner portions extending through respective elongate longitudinally extending slots 135,136 within the body portion 132 of the retriever assembly 130, as can be seen when reading FIGS. 4B, 4C, 3A and 3B when viewed together. This allows the top-cap assembly 110 to slide from the open configuration of FIG. 3A to the closed configuration of FIG. 3B. While for this embodiment of the invention there are two joiner portions 127,129 and two corresponding slots 135,136, in other embodiments of the invention a single joiner portion 127 and corresponding slot 135 may be provided. Is still other embodiments of the invention a three or more joiner portions and corresponding slots may be provided.

Figure 8A:
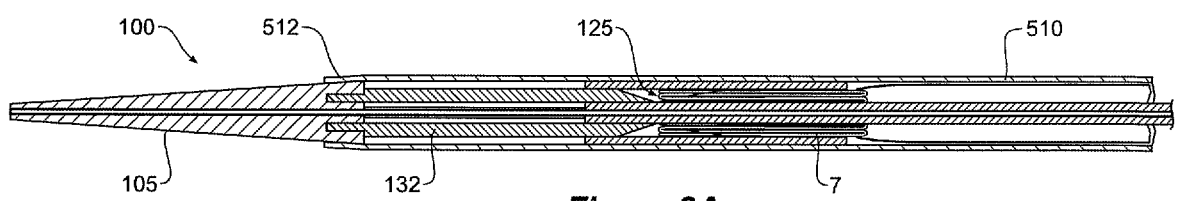
FIGS. 8A, 8B and 8C are cross-sectional views of a proximal end of the device shown in FIG. 1A, in progressive deployment positions.
Figure 8B:
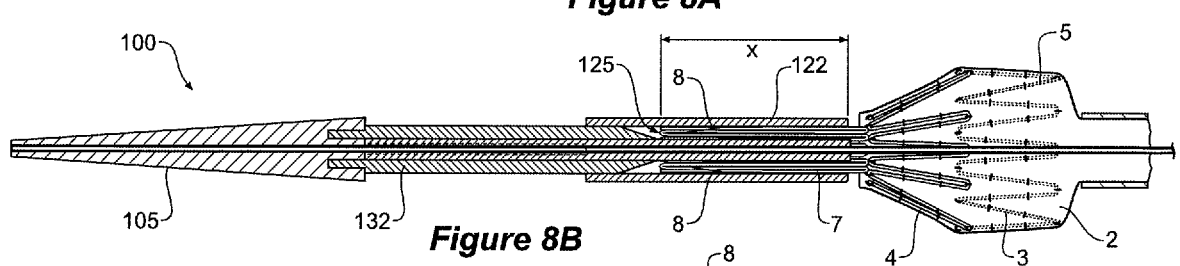

Returning to FIG. 3A, it can be seen that the cavity 125 is able to receive the proximal portion 6 of the endograft 5 (shown in FIG. 2B) in the open configuration, as is clearly shown in the cross-sectional view of FIGS. 8A and 8B. Furthermore FIGS. 8A and 8B show how the cavity 125 holds compressed a length of the exposed stent 7 of the endograft.

The top-cap assembly further comprises a retriever assembly 130 having a body portion 132. This is shown as a separate component in FIG. 4B. The body portion is arranged and constructed to fit within the cavity 125 of the capsule in the closed configuration, as is shown in FIGS. 3A and 3B.

The endovascular delivery device 10 of FIG. 1A also comprises a guide wire catheter 40 extending through the handle assembly 200, the guide wire catheter 40 being affixed at a proximal end thereof to the top-cap assembly 110, and an endograft receiving portion 50 extending distally with respect to the top-cap assembly. The endograft receiving portion 50 is shown in FIG. 2A.

In the closed configuration of the delivery device 10, the cavity 125 is closed by the body portion 132 of the retriever assembly 130. This closed configuration is shown in FIGS. 2A, 2B, and 3B.

Referring to FIGS. 3A, 8A and 8B, it can be seen that the outer tubular portion 122 extends distally beyond the body portion 132 when in the open configuration. This provides good coverage of the proximal portion 6 of the stent-graft/endograft 5. This is particularly important when barbs are provided, such as the barbs 8 shown in FIGS. 2B and 8C. It also allows the cavity 125 to hold compressed a length x of the exposed stent 7 of the endograft, thereby providing precise control during the deployment sequence. Length x is illustrated in FIGS. 1A and 8B. Length x is chosen such that the external stent 7 is compressed not just at its proximal most end, but along a length x.

Referring to FIG. 3A, the extent to which the outer tubular portion 122 extends distally beyond the body portion 132 can be seen. The outer tubular portion 122 extends distally beyond the body portion 132 for a length L. This provides an L/D of about 3, when in the open configuration, where D is an internal diameter of the cavity as is marked on FIG. 3A. In other embodiments, L/D may be different and may be less than or more than 3. Non-limiting examples of L/D include 0.5, 1, 2, 5 and 10, when in the open configuration.

In the embodiment of the invention shown in FIGS. 1A, 1B, 2A, 2B, 3A, 3B, 4A, 4B and 4C, the body portion 132 includes a tapered distal end portion 113. This is most clearly shown in FIG. 4B. This tapered distal end portion 113 provides a lead-in surface. This lead-in surface provides a lead-in for the entire top-cap assembly 110 when in the position shown in FIGS. 2B and 3B. With the embodiments shown in the drawings, and in particular FIG. 3B, the lead-in surface of the tapered distal end portion 113 includes a frusto-conical portion. In other embodiments, not shown, the lead-in surface may be bullet-shaped or any suitable shape so as to provide a lead-in for the top-cap assembly 110 as it is retracted distally away from the heart back towards the introduction site. The external surface of tapered distal end portion 113 is relatively straight forward in its shape. There are no large steps in the diameter that could catch on a deployed stent-graft (or other prosthesis) or on any parts of the body including its vascular system. This provides advantages over many prior art devices.

Referring to FIGS. 5A to 5D, 6A and 6B together, a second embodiment of the invention is shown. In this embodiment, it can be seen that the endovascular delivery device 10 again comprises: a handle assembly 200 at a distal end 18 thereof and a top-cap assembly 110 at a proximal end 12 thereof. The top-cap assembly has an open configuration and a closed configuration shown in FIGS. 7A and 7B respectively. The top-cap assembly comprises: a capsule 120 comprising an inner portion 128 and an outer tubular portion 122 and defining a cavity 125 within the outer tubular portion, as is most clearly shown in FIGS. 3A and 6. Again, with this embodiment, the cavity 125 is of an annular shape.

The top-cap assembly this embodiment, as shown in FIGS. 6A and 6B, again further comprises a tip 105, the tip tapering in a proximal direction.

As in the first embodiment of the invention, the inner portion 128 and the outer tubular portion 122 are joined by radially extending joiner portions 127 and 129, the joiner portions extending through respective elongate longitudinally extending slots 135,136 within the body portion 132 of the retriever assembly 130, as can be seen when reading FIGS. 4B, 4C, 6A and 6B when viewed together. This allows the top-cap assembly 110 to slide from the open configuration of FIG. 6A to the closed configuration of FIG. 6B.

Returning to FIG. 6A, it can be seen that the cavity 125 is able to receive the proximal portion 6 of the endograft 5 (shown in FIG. 5B) in the open configuration, as is clearly shown in the cross-sectional view of FIGS. 8A and 8B.

The top-cap assembly further comprises a retriever assembly 130 having a body portion 132. This is shown as a separate component in FIG. 4B (being the same component of the first embodiment of the invention. The body portion is arranged and constructed to fit within the cavity 125 of the capsule in the closed configuration, as is shown in FIGS. 6A and 6B.

Figure 5A:
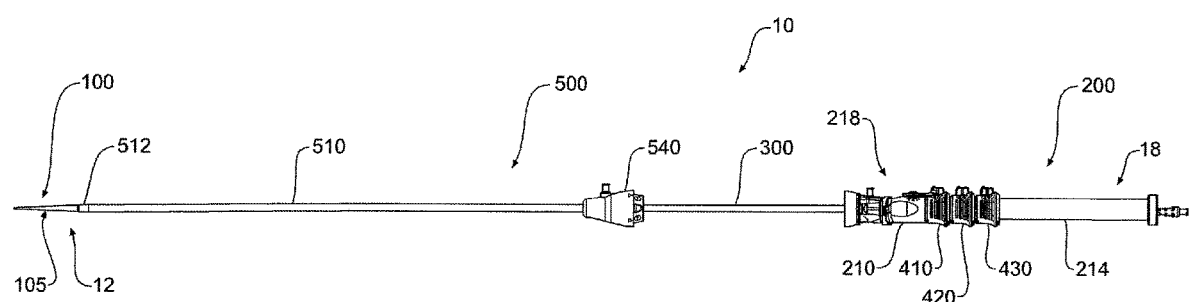
FIG. 5A shows a second embodiment of an endoluminal delivery device according to the invention in a side view.
Figure 5B:
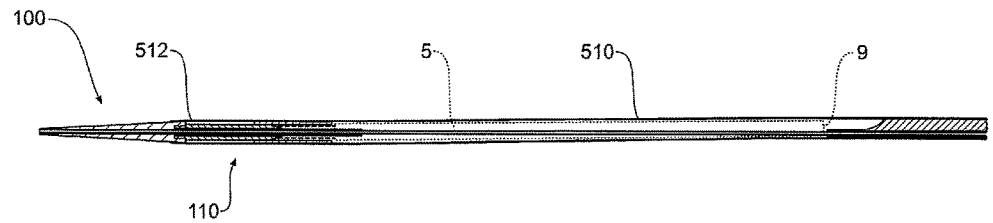
FIG. 5B shows a proximal end of the device of FIG. 5A.

As for the first embodiment of the invention, the endovascular delivery device 10 of FIG. 5A also comprises a guide wire catheter 40 extending through the handle assembly 200, the guide wire catheter 40 being affixed at a proximal end thereof to the top-cap assembly 110, and an endograft receiving portion 50 extending distally with respect to the top-cap assembly. The endograft receiving portion 50 is shown in FIG. 5D.

In the closed configuration of the delivery device 10, the cavity 125 is closed by the body portion 132 of the retriever assembly 130. This closed configuration is shown in FIGS. 5B, 6B, 7B and 8C.

Referring to FIG. 6A, the extent to which the outer tubular portion 122 extends distally beyond the body portion 132 can be seen. As for the second embodiment of the invention, the outer tubular portion 122 extends distally beyond the body portion 132 for a length L. This provides an L/D of about 3, when in the open configuration, where D is an internal diameter of the cavity as is marked on FIG. 6A. In other embodiments, L/D may be different and may be less than or more than 3. Non-limiting examples of L/D include 0.5, 1, 2, 5 and 10, when in the open configuration.

Figure 12:
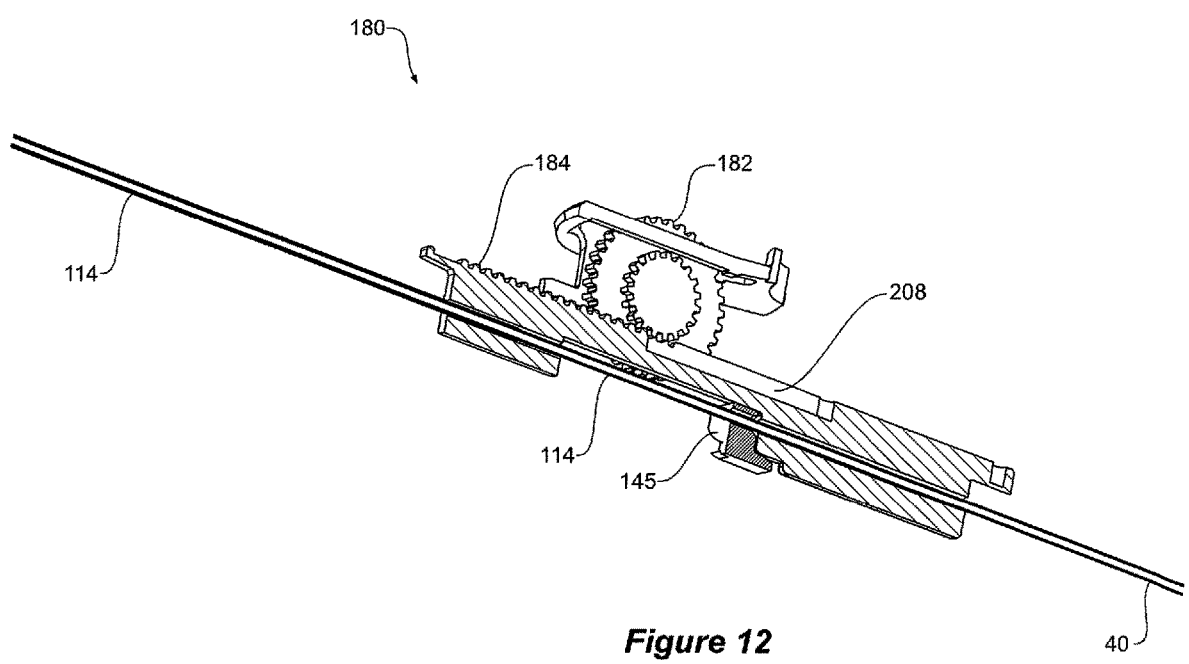
FIG. 12 is a similar view to that of FIG. 10, but is a cross-sectional view.
Figure 13:
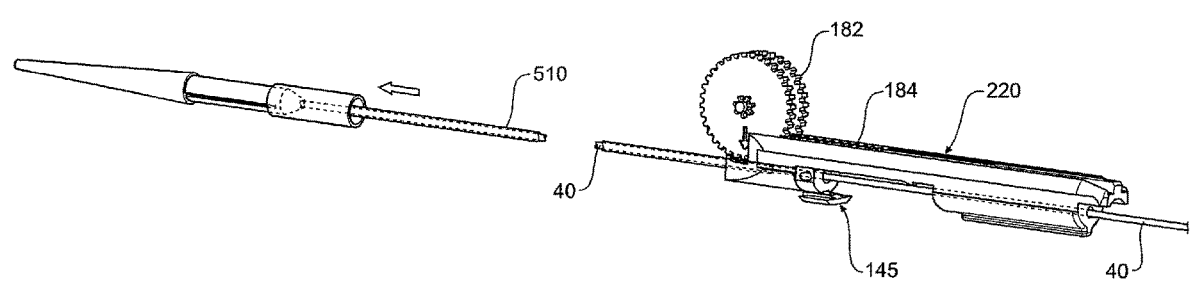
FIG. 13 is a similar view to that of FIG. 10, but shows the proximal end of the device including the top-cap assembly.
Figures 16, 16A:
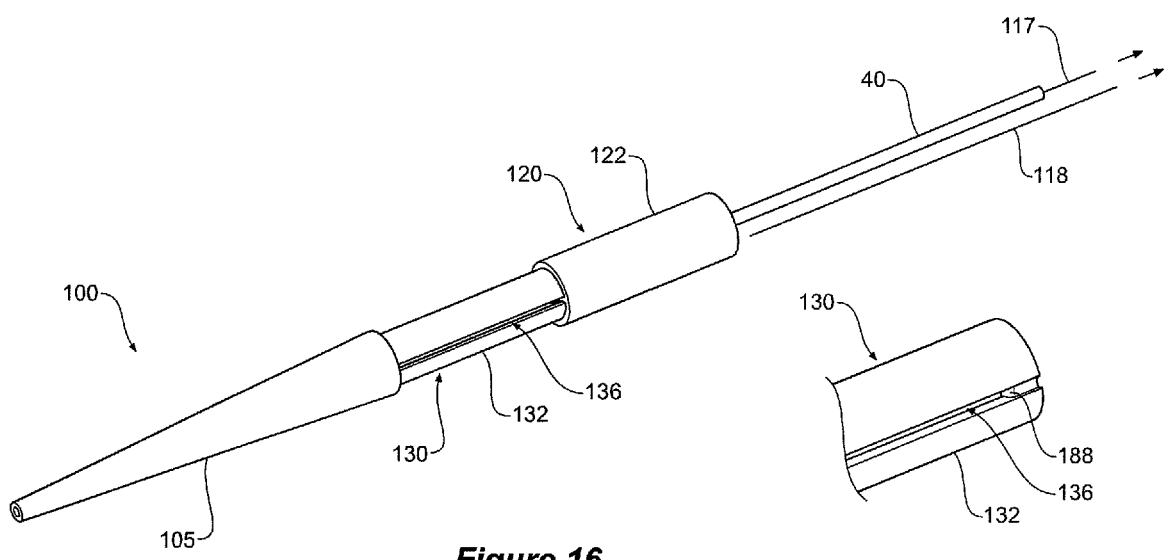
FIG. 16 is similar to FIG. 14, but shows a variant to the capsule 120 where the inner portion 128 does not extend outside of the outer tubular portion.
FIG. 16A is a detailed view of a portion of a retriever assembly shown in FIG. 16.

Again turning to FIGS. 6A and 6B, it can be seen that a connector 114 extending distally from the top-cap assembly 110 towards the handle assembly is provided. The other end of the connector 114 is shown in FIGS. 9A, 9B, 9C and 9D as well as in FIGS. 10 and 12. In the embodiment illustrated in the afore-mentioned figures, the connector is in the form of an elongate tube coaxially mounted over the guide wire catheter 40. The elongate tube may take any appropriate form. For instance, the tube may be a thin walled plastics tube (made for instance of polyetheretherketone or PEEK) or metal tube made of stainless steel or Nitonol (a metal alloy of nickel and titanium, where the two elements are present in roughly equal atomic percentages) for instance. The elongate tube will need to have sufficient resistance to compressive forces so as to be able to transmit motion from the handle assembly 200 to the top-cap assembly 110 so as to slide the top-cap assembly 110 from its open configuration shown in FIG. 6A to its closed configuration shown in FIG. 6B. Many possible constructions that are to transmit or convey a pushing force may be suitable for the connector 114.

Figure 7A:
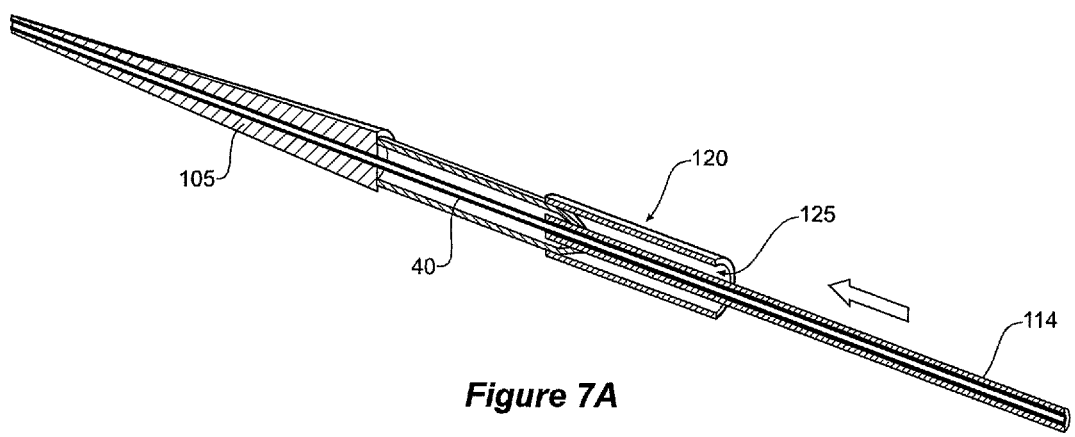
FIGS. 7A and 7B are similar views to those of FIGS. 6A and 6B, but are cross-sectional views.
Figure 7B:
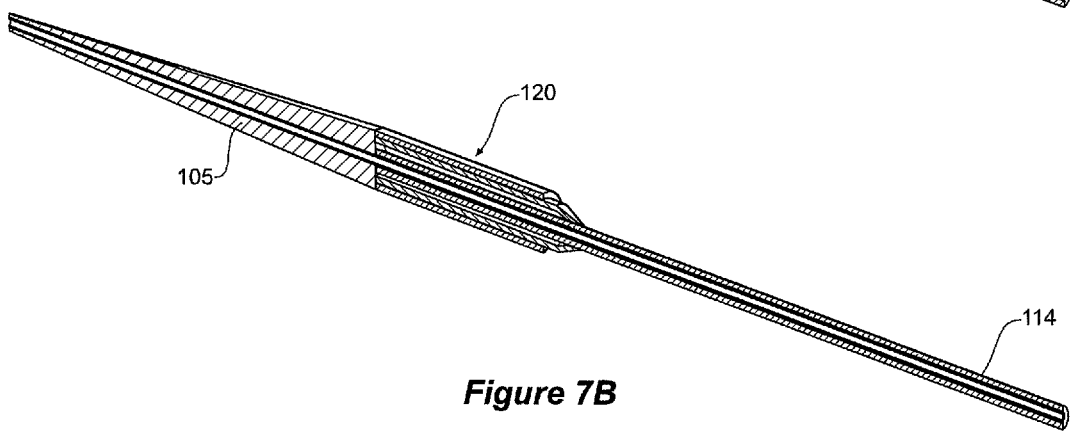

Turning to FIG. 6C, a detailed isometric cross-sectional portion of the connector 114 and adjacent components of the tip assembly 100 are illustrated. More specifically, it can be seen that the inner portion 128 of the capsule 120 extends distally from the joiner portions 127 and 129 and then tapers in and joins the connector tube 114. This allows different materials to be used for the relatively long elongate connector 114 and the inner portion 128 of the capital 120. In other embodiments, the connector tube 114 may be integral with the inner portion 128 of the capsule 120. An example of this is shown in FIGS. 7A and 7B.

Figure 1B:
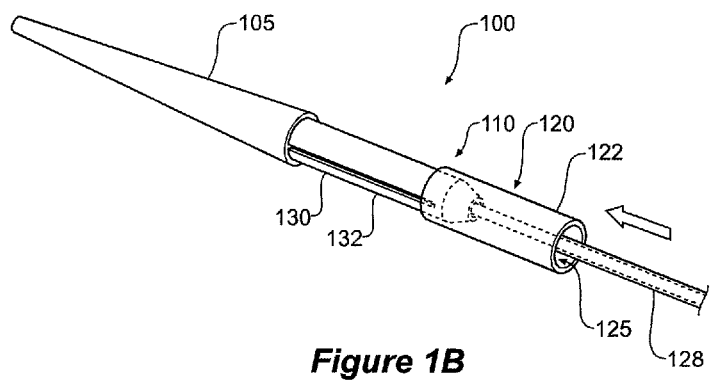
FIG. 1B shows a proximal end of the device of FIG. 1A.

A further embodiment of the invention comprises the endovascular delivery device 10 as described above mounted within a sheath assembly 500 of the type shown in FIGS. 1A and 2A. The sheath assembly 500 comprises a seal housing assembly 540 and a sheath 510 extending proximally from the seal housing assembly 540. As can be seen in FIGS. 1B and 2B, the proximal end 512 of the sheath 510 is retractable from a position shown in FIGS. 1A and 1B over the stent graft 5 to a position shown in FIGS. 2A and 2B retracted back so as to expose the stent graft 5.

Referring now to FIG. 8A, which is a detailed cross-sectional view of the tip assembly 100 while in the position shown in FIGS. 1A and 1B, it can be seen that the proximal end 512 of the sheath 510 completely covers the top-cap assembly 110 and mates with the tip 105. When the sheath assembly 500 is retracted to the position shown in FIG. 5A, the proximal portion 6 of the stent graft 5 remains captive within the capsule 120, as is shown clearly in the cross-sectional view of FIG. 8B. The capsule 120 and in particular the outer tubular portion 122 covers and holds compressed the barbs 8 on the proximal portion 6 of the stent graft 5. This allows the surgeon to continue to make fine adjustments to the position of the stent graft 5 even after the sheath has been withdrawn to the position shown in FIG. 8B.

Figure 8C:
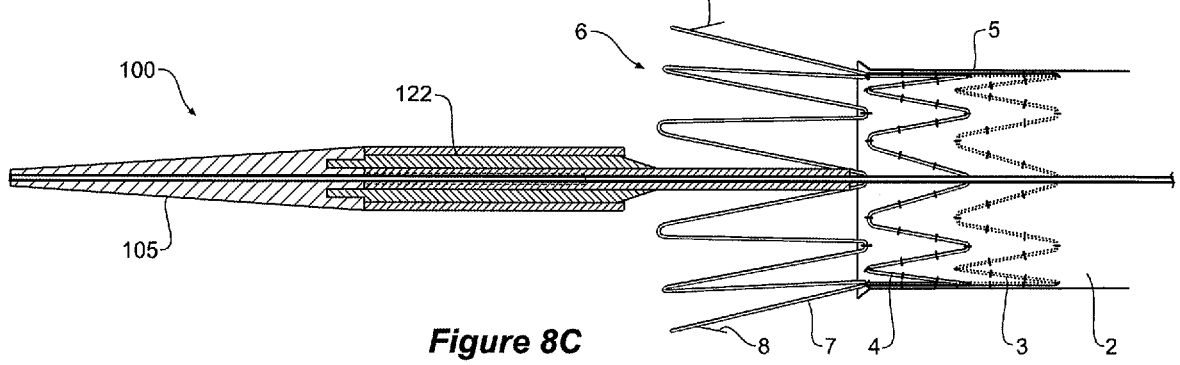

Once the surgeon wishes to release the proximal end of the sent graft 5, he/she is able to advance the capsule 120 and its outer tubular portion 122 to the position shown in FIG. 8C thereby releasing the barbs 8. It should be noted that in the transition between the positions shown in FIGS. 8A, 8B and 8C, the tip 105 does not move. This is in contrast to many prior art devices where the tip 105 is advanced in a proximal direction (moving upstream or towards the heart) in order to release the proximal end of the graft or at least in order to move the top-cap assembly into an atraumatic retractable condition.

Figures 9A, 9B:
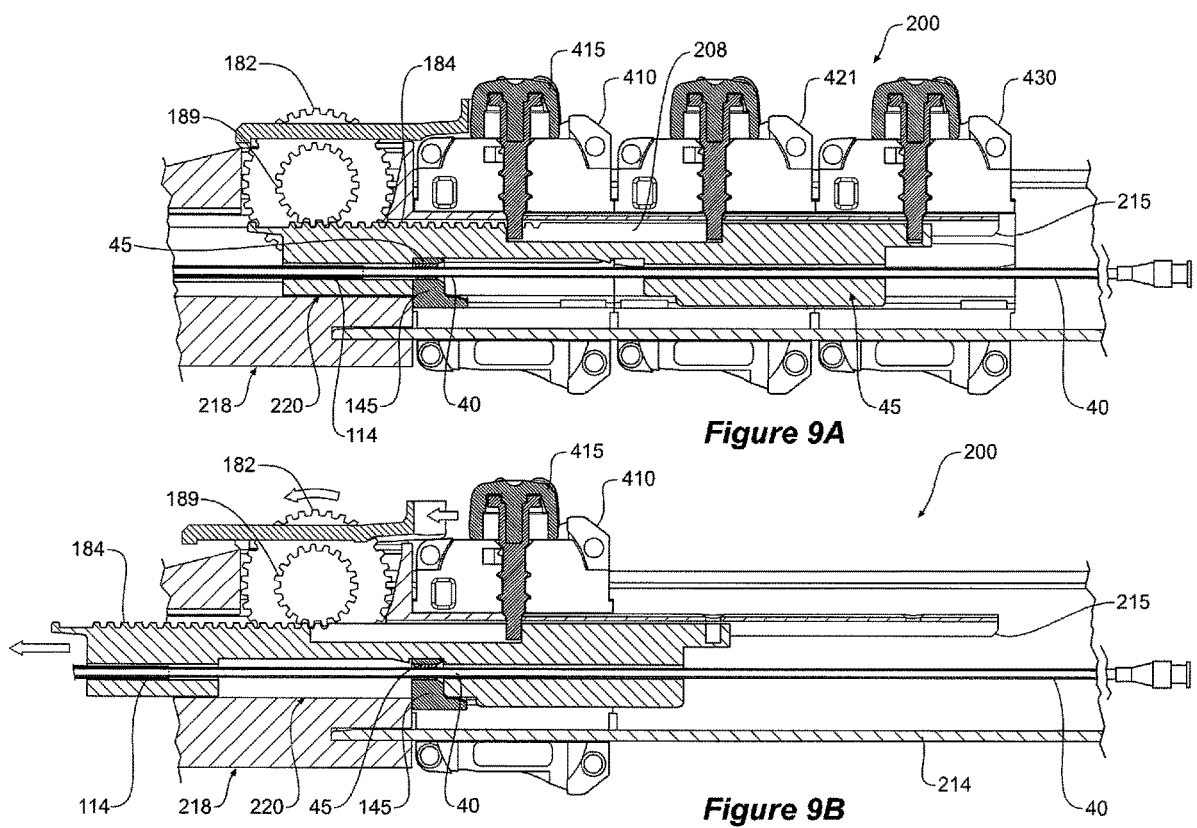
FIGS. 9A, 9B, 9C and 9D are detailed cross-sectional views of the handle assembly of FIG. 1A in progressive deployment positions.
Figure 9C:
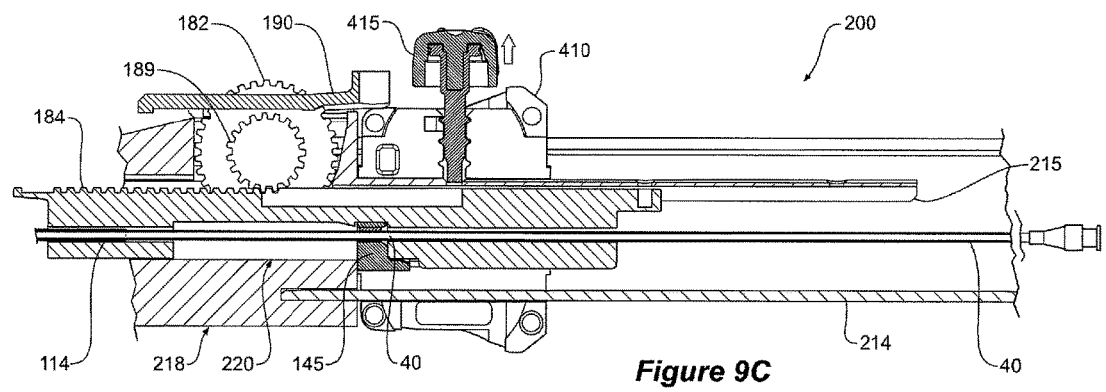
Figure 9D:
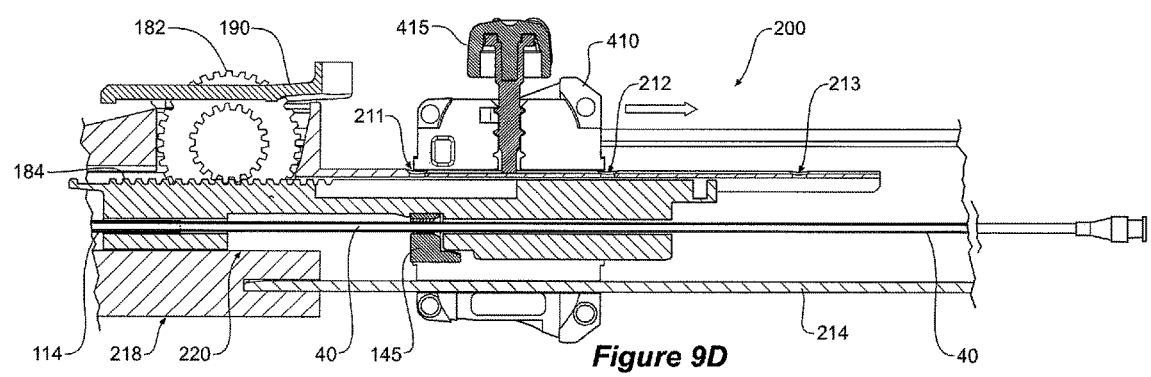

Referring to FIGS. 9A, 9B, 9C and 9D, the handle assembly 200 is shown in detailed cross-sectional views. Referring first to FIG. 9A, it can be seen that the handle assembly 200 includes a body portion 218 inside which an inner portion 220 slides.

Figure 5C:
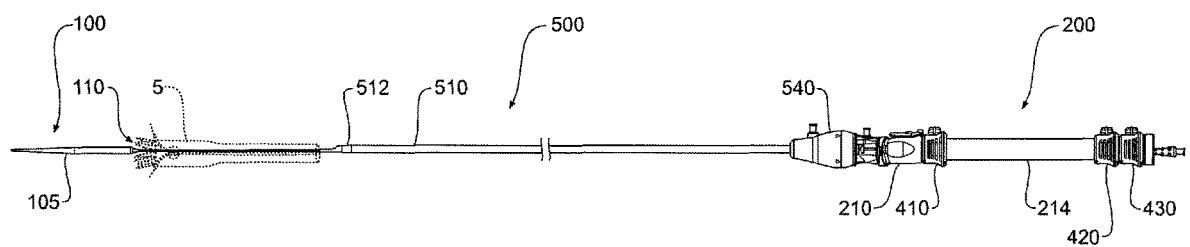
FIG. 5C is a similar side view to that of FIG. 5A but showing a sheath assembly in a retracted position.
Figure 5D:
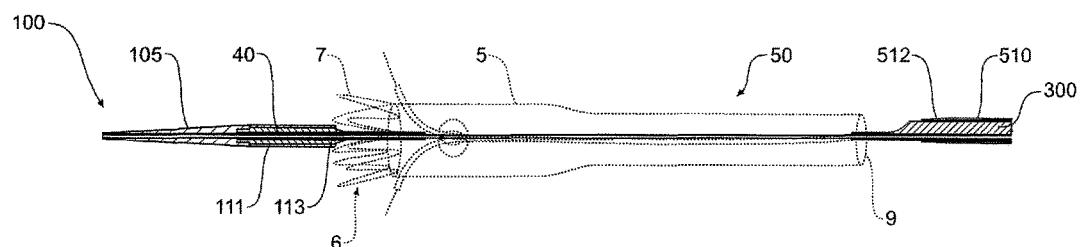
FIG. 5D shows a proximal end of the assembly of FIG. 5C.

Referring to FIGS. 5A and 5C, a tip assembly slider 410 is shown. The tip assembly slider 410 is operably connected to the inner handle portion 220 such that distal sliding movement of the tip assembly slider 410 slides the tip assembly 100 towards the pusher catheter 300. However, this cannot occur until after the top-cap assembly has been advanced as will be clear when reviewing the Figures and reading the below.

A tip assembly actuator 182, in the form of a thumbwheel, shown in FIG. 9A, is operably connected to the inner handle portion 220. The thumbwheel 182 drives a rack 184. The rack 184 is slideably drivable by the thumbwheel 182 in a proximal direction. The thumbwheel 182 is actuatable to move the inner handle portion 220 proximally with respect to the outer handle portion 210 thereby actuating the tip assembly 100 from the first configuration shown in FIG. 6A to the second configuration shown in FIG. 6B. It is only after this has occurred that the tip assembly slider 410 can be moved from its position shown in FIG. 9C to its position shown in FIG. 9D, thereby sliding the tip assembly 100 towards the pusher catheter 300 ready for withdrawal.

While many different handle actuators may be suitable for use with variants of the first and second embodiments of the device 10 shown in FIGS. 1A and 5A, the handle assembly herein described and described in more detail in the applicant's earlier filed Australian Patent application no. AU2017904881 titled An Endograft Delivery Device Assembly may be used with the modifications shown in FIGS. 9A, 9B, 9C and 9D. This application no. AU2017904881 is hereby incorporated by reference into the present application.

The modifications shown in FIGS. 9A, 9B, 9C and 9D (compared to the handle assembly herein described and described in more detail in the applicant's earlier filed Australian Patent application no. AU2017904881) include termination and connection of the terminal connector 114 into the proximal end of the inner handle portion 220 as is shown clearly in the isometric views of FIGS. 10 and 12. The guide wire catheter 40 is joined to a guide wire catheter receiver 145 which is part of the tip assembly slider 410, as is shown most clearly in FIGS. 11A and 11B when viewed with FIGS. 9A to 9D. A guide wire catheter joiner 45 in the form of adhesive is shown in FIGS. 9A, 11A and 11B. In other embodiments, not shown, other joiners including compression fittings may be used instead.

The connector 114 is connected to the inner handle portion 220, as is shown in FIGS. 9A to 9D.

Turning now to FIGS. 11A and 11B, it can be seen that the guide wire catheter receiver 145, which is part of the tip assembly slider 410, sits within a connector receiver portion 204 of the inner handle portion 220. It can be seen that the receiver portion 204 has two extreme positions. The first position is shown in FIGS. 9A and 11A. The second position is shown in FIGS. 9B and 11B.

The connector receiver portion 204 locks to guide wire catheter receiver 145 when the inner handle portion 220 moves to the proximal position shown in FIGS. 9B and 11B. While various locking arrangements may be used, with the first embodiment of the invention shown, the connector receiver portion 204 comprises a ramped portion 205 and a shoulder portion 206. The shoulder portion 206 abuts a surface 116, shown in FIG. 11A, of the guide wire catheter receiver 145 when the inner handle portion 220 is in the proximal position.

A third embodiment of the invention is shown in FIGS. 14, 15, 15A, 16 and 16A. This embodiment of the invention is similar to the first and second embodiments described above. However, the connector 114 in the form of an elongate tube of the first embodiment, such as is clearly shown in FIGS. 6A, 6B and 6C, is replaced by a connector wire or a plurality of wires 117,118 that together form a connector as is shown in FIGS. 14, 15, 15A, 16 and 16A. In FIG. 15, the retriever assembly 130 is omitted for clarity and so as to show the routing of the wires 117 and 118.

FIG. 14 shows a tip assembly 100 of the third embodiment of the invention at an end of the device of the type shown in FIG. 1A in an isometric view. In this view, the tip assembly has a top-cap assembly 110 in an open configuration. FIG. 15 shows the top-cap assembly 110 in an closed configuration and FIG. 15A is an end view of the capsule shown in FIG. 15.

Figure 20A:
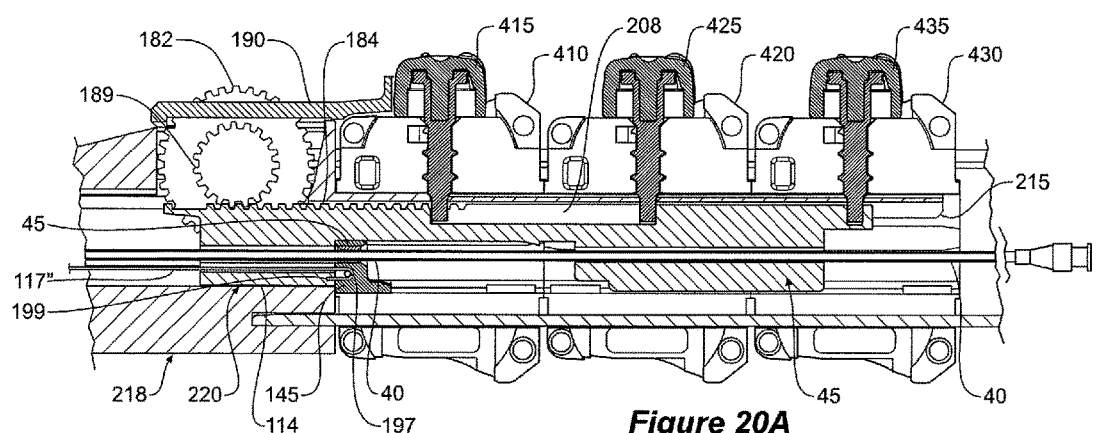
FIGS. 20A, 20B, 20C and 20D are detailed cross-sectional views of the handle assembly of the third embodiment shown in FIG. 14 in progressive deployment positions.

Referring now to FIGS. 16, 16A, 17A and 17B, it can be seen that the connector of the third embodiment of the invention, in the form of a wire 117, or wires 117,118 is mounted adjacent the guide wire catheter 40 and has a distal portion(s) 117",118" connected to the handle assembly. The connection to the handle assembly is shown in FIG. 20A.

Figure 17A:
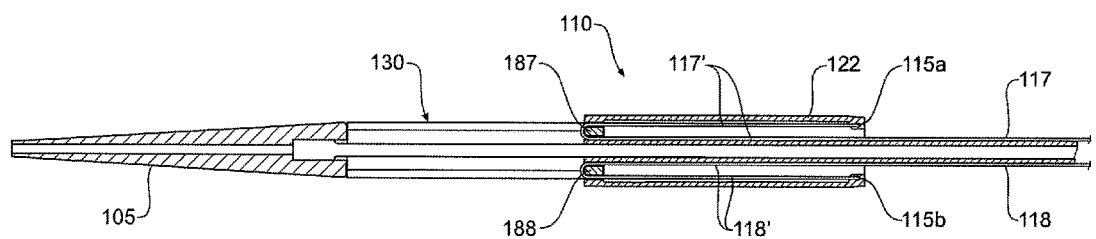
FIG. 17A is a cross-sectional side view of the device shown in FIG. 16 in its open configuration.
Figure 17B:
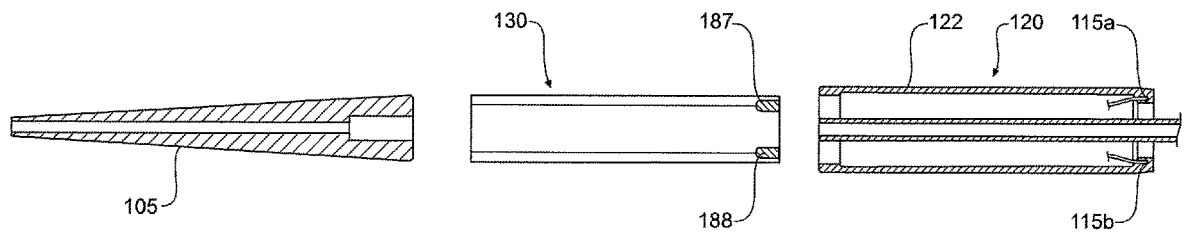
FIG. 17B is an exploded version of FIG. 17A, with pull wires mostly removed for clarity.

The connector also has a proximal portion 117' and 118' looped over corresponding rounded return surface(s) 187, 188 on the retriever assembly of the top-cap assembly 110 and extending distally back to the capsule 120. The rounded return surface 188 is most clearly shown in the perspective view of FIG. 16A and in the cross-sectional view of FIG. 17A and in the cross-sectional view of 17B. FIGS. 17A and 17B also show the ends 115a and 115b of proximal portions 117' and 118' connecting to the distal end of the capsule 120. In other embodiments, a small pulley or a number of small pulleys may be provided to replace the return surface(s).

Figure 17C:
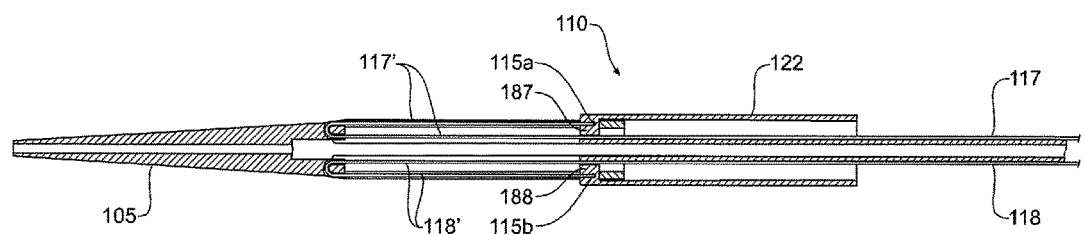
FIG. 17C is a similar cross-sectional side view to that of FIG. 17A, but shows the device of FIG. 16 in its closed configuration.

FIGS. 17A and 17B on the one hand, and FIGS. 17B and 17C on the other hand, show two variants of the third embodiment of the invention. With the variant shown in FIGS. 17A and 17B, the capsule 120 is pulled proximally from its distal end and in the variant shown in FIGS. 17C and 17D, the capsule 120 is pulled proximally from its proximal end. In FIG. 17B, most of the proximal portions 117' and 118' of the wires are omitted for clarity.

Figure 17D:
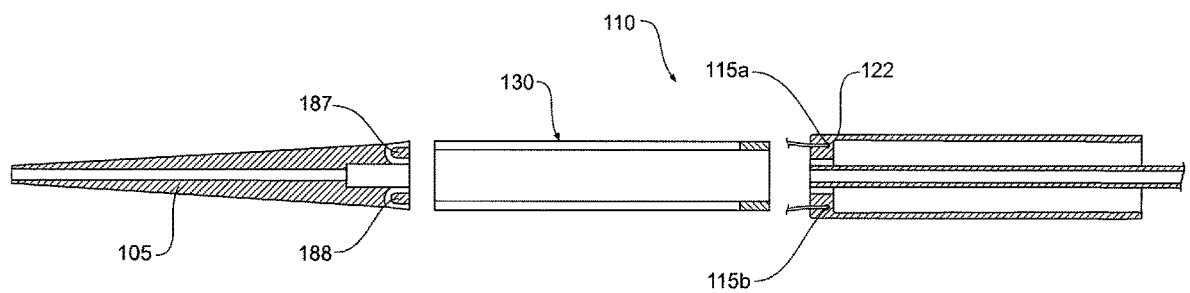
FIG. 17D is an exploded version of FIG. 17C, with pull wires mostly removed for clarity.

FIG. 17D is an exploded version of FIG. 17C and shows the rounded return surfaces 187 and 188 of the second variant of the third embodiment of the invention more clearly. FIGS. 17C and 17D also show the ends 115a and 115b of the wires 117' and 118' connecting to the proximal end of the capsule 120. In FIG. 17D, most of the proximal portions 117' and 118' of the wires are omitted for clarity.

Referring again to the cross-sectional side views of FIGS. 17A to 17D, the wire 117, or wires 117,119, are joined to the capsule 120 at their proximal portions 117',118' such that as the handle assembly 200 creates a pulling displacement of the proximal portion(s) 117',118' of the wire(s) 117,118, the capsule 120 is drawn over the body portion 132 of the retriever assembly 130. This pulls the top-cap assembly 110 from the open configuration shown in the cross-sectional side view of FIG. 17A towards its closed configuration shown in the side view of FIG. 19.

Referring to FIG. 16 again, this is a similar view to FIG. 14, but shows a variant to the capsule 120 where the inner portion 128 does not extend outside of the outer tubular portion 122.

Figure 18:
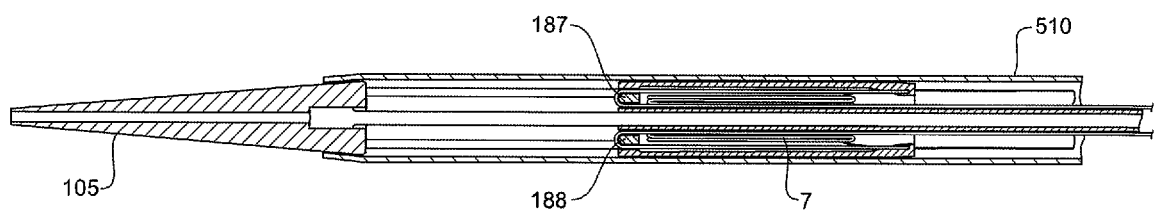
FIGS. 18 and 19 are similar to those of FIGS. 17A and 17B, but show the proximal end of the stent-graft as it is positioned before and after release respectively.
Figure 19:
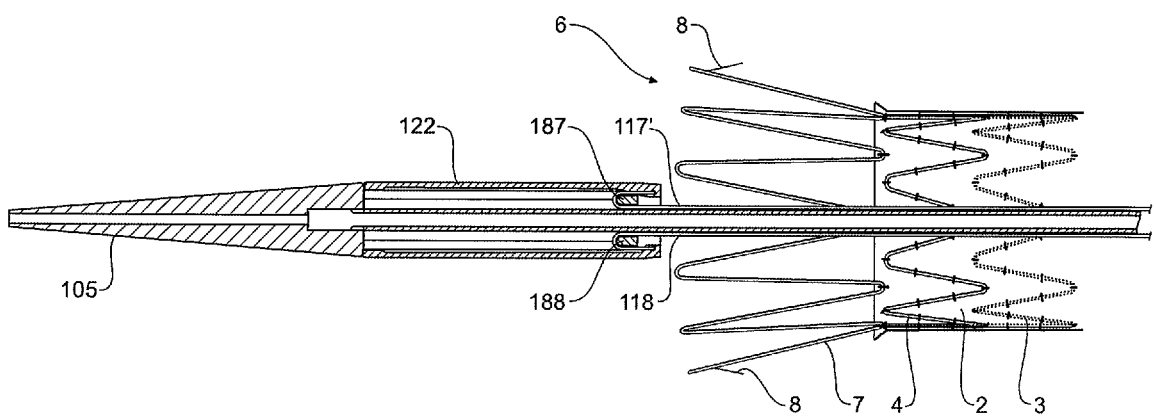

Now referring to FIGS. 18 and 19, the proximal end 6 of the stent-graft 5 is shown as it is positioned before and after release respectively.

In FIG. 18 the sheath 510, being the same as the sheath 510 shown in FIGS. 1A, 1B, 2A and 2B is shown in its positon over the stent-graft 5. In FIG. 19, the sheath 510 has been retracted and subsequently the outer tubular portion 122 of the capsule 120 has been advanced by the pulling displacement of the proximal portion(s) 117',118' of the wire(s) 117,118.

FIGS. 20A, 20B, 20C and 20D are detailed cross-sectional views of the handle assembly of the third embodiment shown in FIG. 14 in progressive deployment positions. Referring first to FIG. 20A, it can be seen that the handle assembly 200 includes a body portion 218 inside which an inner portion 220 slides (in much the same way as is shown in FIG. 9A relating to the handle assembly of the first embodiment of the invention). A tip assembly actuator 182, in the form of a thumb wheel, is operably connected to the inner handle portion 220. The thumbwheel 182 drives a rack 184. The rack 184 is slideably drivable by the thumbwheel 182 in a proximal direction. The thumbwheel 182 is actuatable to move the inner handle portion 220 proximally with respect to the outer handle portion 210 thereby actuating the tip assembly 100 from the first configuration shown in FIG. 3A to the third configuration shown in FIG. 3B.

Again, while many different handle actuators may be suitable for use with variants of the third embodiment of the device 10 shown in FIG. 14, the handle assembly herein described and described in more detail in the applicants earlier filed Australian Patent application no. AU2017904881 titled An Endograft Delivery Device Assembly may be used with some modifications.

Figure 20B:
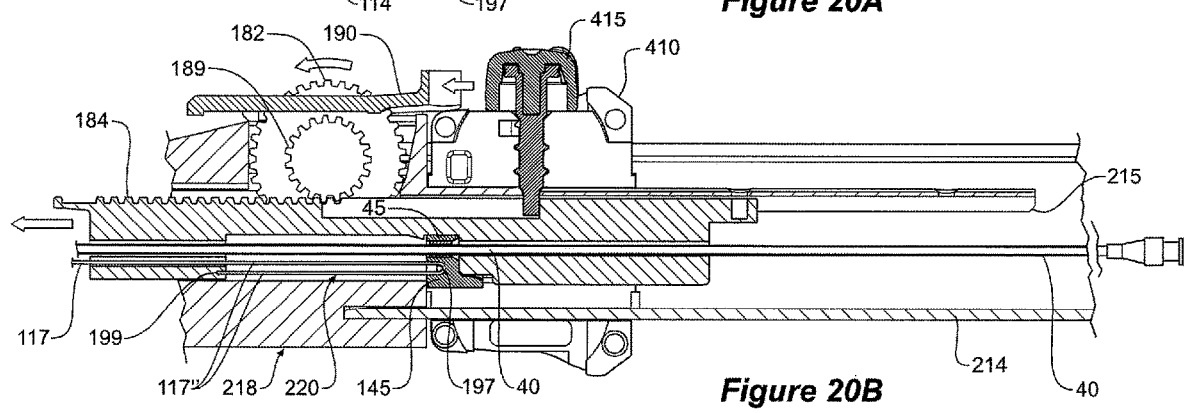
Figure 20C:
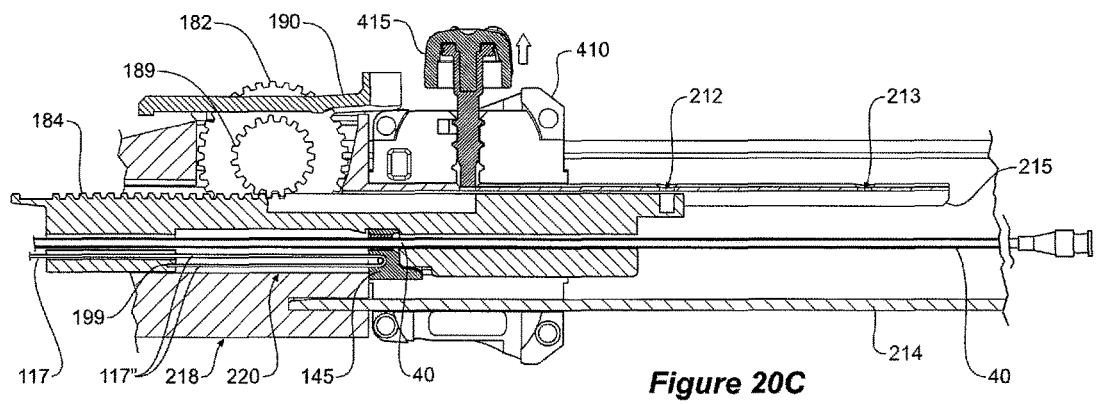
Figure 20D:
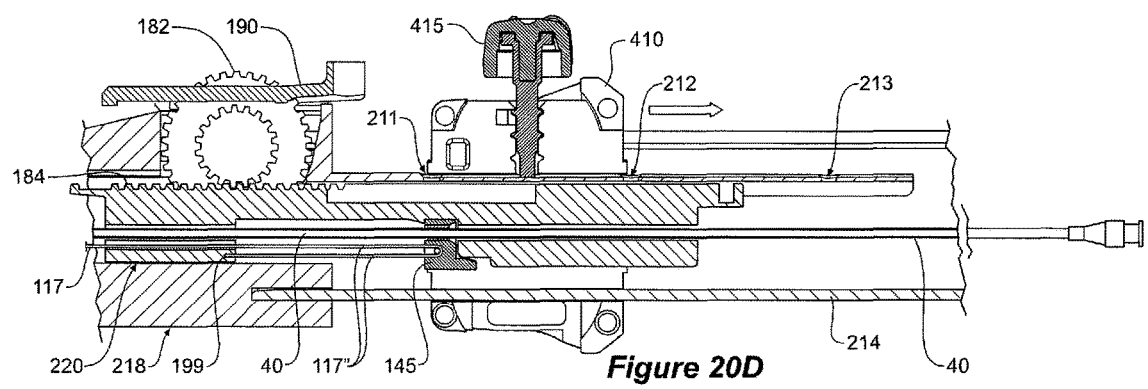

The modifications shown in FIGS. 20A, 20B, 20C and 20D (compared to the handle assembly herein described and described in more detail in the applicants earlier filed Australian Patent application no. AU2017904881) include termination and connection of the wires 117,118 into the proximal end of the inner handle portion 220 as is described in more detail below. Also, the guide wire catheter 40 is joined to a guide wire catheter receiver 145 which is part of the tip assembly slider 410, as is shown in most clearly in FIGS. 20A and 20B. A guide wire catheter joiner in the form of adhesive 45 is shown in FIGS. 20A and 20B. In other embodiments, not shown, other joiners including compression fittings may be used instead.

Wire 117 forms a connector connects to the inner handle portion 220, as is shown in FIGS. 20A, 20B, 20C and 20D. The distal end 117" of the wire 117 loops around a rounded return surface 197 within the guide wire catheter receiver 145 which is a part of tip assembly slider 410 and terminates within the inner handle portion 220 at a terminal end 199. As a result, as the inner handle portion 220 advances proximally form its position shown in FIG. 20A to its position shown in FIG. 20B, the wire 117 is pulled distally thereby pulling the top-cap assembly 110 from the open configuration shown in the cross-sectional side views of FIG. 17A or 17B and the view of FIG. 18 towards its closed configuration shown in the side view of FIG. 19.

Turning now to FIGS. 20A and 20B, it can be seen that the guide wire catheter receiver 145 which is part of the tip assembly slider 410 sits within a connector receiver portion 204 of the inner handle portion 220. It can be seen that the receiver portion 204 has two extreme positions. The first position is shown in FIG. 20A and the second position is shown in FIG. 20B.

The connector receiver portion 204 locks to guide wire catheter receiver 145 when the inner handle portion 220 moves to the proximal position shown in FIGS. 9B and 11B (of the first embodiment). While various locking arrangements may be used, with the third embodiment of the invention shown, the connector receiver portion 204 comprises a ramped portion 205 and a shoulder portion 206. The shoulder portion 206 abuts a surface 116, shown in FIG. 11A, of the guide wire catheter receiver 145 when the inner handle portion 220 is in the proximal position.

In the third embodiment of the invention shown in FIGS. 14, 15 and 6, the body portion 132 is shown without a tapered distal portion of the type shown in FIGS. 3B and 5 as 113. This arrangement may be suitable for some applications. However, the third embodiment of the invention may include a tapered distal portion 113 of the type shown in in FIGS. 3B and 5 which provides a better lead-in surface.

With all of the embodiments of the invention described above, there is no need to provide for mechanical locking solutions for the retriever assembly 130 as is the case with many prior art devices. This is because the retriever assembly 130, and its tapered distal end portion 113 when provided, cannot be pushed back into the cavity behind it during retrieval of the delivery device.

Also in tortuous anatomy it is possible that the retrieval cone/tip of prior art delivery devices could fail (eg. by popping out of the top cap). Embodiments of the invention are able to eliminate this potential.

A further advantage of embodiments of the invention is that, while with many prior art delivery devices barbed end stents are released by moving the tip and top cap proximally (further up into the aorta), with embodiments of the invention, there is no need to move the tip at all. Instead it is just the capsule 120 that moves. This is clearly illustrated in FIGS. 8A to 8C.

A still further advantage of embodiments of the invention is that loading of an endograft onto the delivery device is made easier given that the tip position stays the same with only the capsule 120 moving.

A still further advantage of embodiments of the invention is only one moving part is required within the tip assembly 100.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The invention claimed is:

1. An endovascular delivery device, for delivering an endograft having an exposed stent, the delivery device comprising:
   a handle assembly at a distal end thereof;
   a top-cap assembly at a proximal end thereof, the top-cap assembly having an open configuration and a closed configuration, the top-cap assembly comprising:
      a capsule comprising an inner portion and an outer tubular portion and defining a cavity within the outer tubular portion, the cavity receiving a proximal portion of the endograft in the open configuration; and
      a retriever assembly having a body portion, the body portion arranged and constructed to fit within the cavity of the capsule in the closed configuration;
   a guide wire catheter extending through the handle assembly, the guide wire catheter being affixed at a proximal end thereof to the top-cap assembly; and
   an endograft receiving portion extending distally with respect to the top-cap assembly,
   whereby in the closed configuration, the cavity is closed by the body portion of the retriever assembly,
   whereby the outer tubular portion extends distally beyond the body portion when in the open configuration to hold compressed a length of the exposed stent of the endograft,
   whereby movement of the capsule from the open configuration towards the closed configuration yields expansion of the stent, and
   wherein the inner portion and the outer tubular portion are joined by a radially extending joiner portion, the joiner portion extending through at least one elongate longitudinally extending slot within the body portion of the retriever assembly, thereby allowing the top-cap assembly to slide from the open configuration to the closed configuration.

2. The device as claimed in claim 1, wherein an extent to which the outer tubular portion extends distally beyond the body portion for a length L such that L/D is at least 2, when in the open configuration, where D is an internal diameter of the cavity.

3. The device as claimed in claim 2 such that L/D is at least 3, when in the open configuration.

4. The device as claimed in claim 1, wherein the body portion of the retriever assembly comprises a tapered distal end portion, the tapered distal end portion tapering in a distal direction.

5. The device as claimed in claim 1 comprising a connector extending from the top-cap assembly to the handle assembly, the connector arranged to transfer motion from the handle assembly to the top-cap assembly so as to slide the top-cap assembly from its open configuration to its closed configuration.

6. The device as claimed in claim 5, wherein the connector comprises an elongate tube co-axially mounted over the guide wire catheter.

7. The device as claimed in claim 1, wherein the proximal portion of the endograft comprises a plurality of barbs.

8. The device as claimed in claim 1, wherein barbs of the endograft are covered by the outer tubular portion when in the open configuration.

9. The device as claimed in claim 1, wherein the top-cap assembly comprises a tip, the tip tapering in a proximal direction.

10. The device as claimed in claim 1, wherein the guide wire catheter is attached to a proximal end of a tip of the top-cap assembly.

11. The device as claimed in claim 1 mounted within a sheath assembly, the sheath assembly comprising a seal housing assembly and a sheath extending proximally from the seal housing assembly.

12. The device as claimed in claim 1 mounted within a sheath assembly, wherein the sheath comprises a proximal end that is positionable over the capsule.

13. The device as claimed in claim 1, wherein the cavity is annular in shape.

14. An endovascular delivery device, for delivering an endograft, the endograft having barbs at a proximal portion thereof, the delivery device comprising:
   a handle assembly at a distal end thereof;
   a top-cap assembly at a proximal end thereof, the top-cap assembly having an open configuration and a closed configuration, the top-cap assembly comprising:
      a capsule comprising an inner portion and an outer tubular portion and defining a cavity within the outer tubular portion, the cavity having an annular shape and receiving a proximal portion of the endograft in the open configuration, thereby covering the barbs; and
      a retriever assembly having a body portion, the body portion arranged and constructed to fit within the cavity of the capsule in the closed configuration;
   a guide wire catheter extending through the handle assembly, the guide wire catheter being affixed at a proximal end thereof to the top-cap assembly;
   an endograft receiving portion extending distally with respect to the top-cap assembly,
   whereby in the closed configuration, the cavity is closed by the body portion of the retriever assembly; and
   a connector extending from the top-cap assembly to the handle assembly, the connector arranged to transfer motion from the handle assembly to the top-cap assembly so as to slide the top-cap assembly from its open configuration to its closed configuration, whereby the outer tubular portion extends distally beyond the body portion when in the open configuration, and wherein the inner portion and the outer tubular portion are joined by a radially extending joiner portion, the joiner portion extending through at least one elongate longitudinally extending slot within the body portion of the retriever assembly, thereby allowing the top-cap assembly to slide from the open configuration to the closed configuration.

15. An endovascular delivery device, for delivering an endograft having an exposed stent, the delivery device comprising:

a handle assembly at a distal end thereof;

a top-cap assembly at a proximal end thereof, the top-cap assembly having an open configuration and a closed configuration, the top-cap assembly comprising:

a capsule comprising an inner portion and an outer tubular portion and defining a cavity within the outer tubular portion, the cavity receiving a proximal portion of the endograft in the open configuration; and a retriever assembly having a body portion, the body portion arranged and constructed to fit within the cavity of the capsule in the closed configuration;

a guide wire catheter extending through the handle assembly, the guide wire catheter being affixed at a proximal end thereof to the top-cap assembly; and an endograft receiving portion extending distally with respect to the top-cap assembly, whereby in the closed configuration, the cavity is closed by the body portion of the retriever assembly, whereby the outer tubular portion extends distally beyond the body portion when in the open configuration to hold compressed a length of the exposed stent of the endograft, and wherein the body portion of the retriever assembly comprises a tapered distal end portion, the tapered distal end portion tapering in a distal direction.

16. The device as claimed in claim 15, wherein an extent to which the outer tubular portion extends distally beyond the body portion for a length L such that L/D is at least 2, when in the open configuration, where D is an internal diameter of the cavity.

17. The device as claimed in claim 15, wherein the top-cap assembly comprises a tip, the tip tapering in a proximal direction.

18. The device as claimed in claim 15 mounted within a sheath assembly, wherein the sheath comprises a proximal end that is positionable over the capsule.

19. The device as claimed in claim 15, wherein the cavity is annular in shape.

20. An endovascular delivery device, for delivering an endograft having an exposed stent, the delivery device comprising:

a handle assembly at a distal end thereof;

a top-cap assembly at a proximal end thereof, the top-cap assembly having an open configuration and a closed configuration, the top-cap assembly comprising:

a capsule comprising an inner portion and an outer tubular portion and defining a cavity within the outer tubular portion, the cavity receiving a proximal portion of the endograft in the open configuration; and a retriever assembly having a body portion, the body portion arranged and constructed to fit within the cavity of the capsule in the closed configuration;

a guide wire catheter extending through the handle assembly, the guide wire catheter being affixed at a proximal end thereof to the top-cap assembly;

an endograft receiving portion extending distally with respect to the top-cap assembly, whereby in the closed configuration, the cavity is closed by the body portion of the retriever assembly, whereby the outer tubular portion extends distally beyond the body portion when in the open configuration to hold compressed a length of the exposed stent of the endograft, and whereby movement of the capsule from the open configuration towards the closed configuration yields expansion of the stent; and a connector extending from the top-cap assembly to the handle assembly, the connector arranged to transfer motion from the handle assembly to the top-cap assembly so as to slide the top-cap assembly from its open configuration to its closed configuration, wherein the connector comprises an elongate tube co-axially mounted over the guide wire catheter.

\* \* \* \* \*